United States Patent [19]

Curtin et al.

[11] Patent Number: 5,330,751
[45] Date of Patent: Jul. 19, 1994

[54] ANTIPERSPIRANT AND METHOD OF MAKING SAME

[75] Inventors: Maria A. Curtin, South Easton; Alan M. Phipps, Framingham, both of Mass.

[73] Assignee: The Gilette Company, Boston, Mass.

[21] Appl. No.: 594,349

[22] Filed: Oct. 3, 1990

Related U.S. Application Data

[60] Continuation-in-part of Ser. No. 336,675, Apr. 12, 1989, abandoned, which is a division of Ser. No. 181,564, Apr. 14, 1988, abandoned.

[51] Int. Cl.$^5$ .............. A61K 7/32; A61K 7/34; A61K 7/38; A61K 9/12
[52] U.S. Cl. .............. 424/66; 424/DIG. 5; 424/47; 424/68
[58] Field of Search .............. 424/65, 66, 68

[56] References Cited

U.S. PATENT DOCUMENTS

| 173,607 | 6/1875 | Fehr | 424/65 |
| 2,350,047 | 5/1944 | Klarmann et al. | 424/65 |
| 2,588,389 | 3/1952 | Iler | 252/313 |
| 4,359,456 | 11/1982 | Gosling et al. | 424/68 |

FOREIGN PATENT DOCUMENTS

| 291960 | 11/1988 | European Pat. Off. | 424/65 |
| 337464 | 10/1989 | European Pat. Off. | 424/65 |
| 0366230A | 5/1990 | European Pat. Off. | 424/68 |
| 2000507 | 7/1970 | Fed. Rep. of Germany | 424/65 |
| 52-61239 | 5/1977 | Japan | 424/65 |
| 756475 | 11/1974 | South Africa . | |
| 2027419 | 2/1980 | United Kingdom | 424/68 |
| 2048229 | 12/1980 | United Kingdom | 424/68 |

OTHER PUBLICATIONS

Heilig et al, Chem. Abs., 1969, vol. 73(14):69739x.
Spitzer et al, Chem. Abs., 1974, vol. 85(8):51626w.
Nakano et al, Chem. Abs., 1975, vol. 87(22):172721y.
Encyclopedia of Chem. Technology, 3rd ed., vol. 20, pp. 762-763, 1982.
Grant & Hackh's Chemical Dictionary, 5th ed., pp. 529-530, 1987.
Alexander, J. Am. Chem. Soc., vol. 75, pp. 2887-2888 (1953).
Nelson, Aerosol Age, Oct. 1985, pp. 26-29 and 103.

*Primary Examiner*—Dale R. Ore
*Attorney, Agent, or Firm*—Stephan P. Williams

[57] ABSTRACT

Antiperspirant effectiveness of basic aluminum chloride is increased by mixing it with monosilicic acid in aqueous solution. The product can be dried to a solid, and the antiperspirant effectiveness does not decrease in contact with water. The product can also be characterized by size exclusion chromatography of its approximately 10% by weight aqueous solution. Zirconyl hydroxy chloride may also be present.

9 Claims, 7 Drawing Sheets

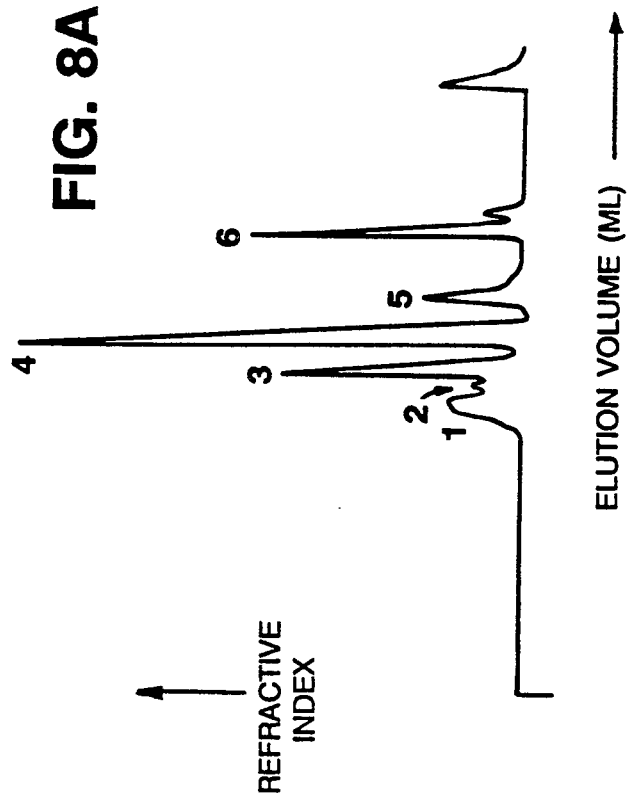
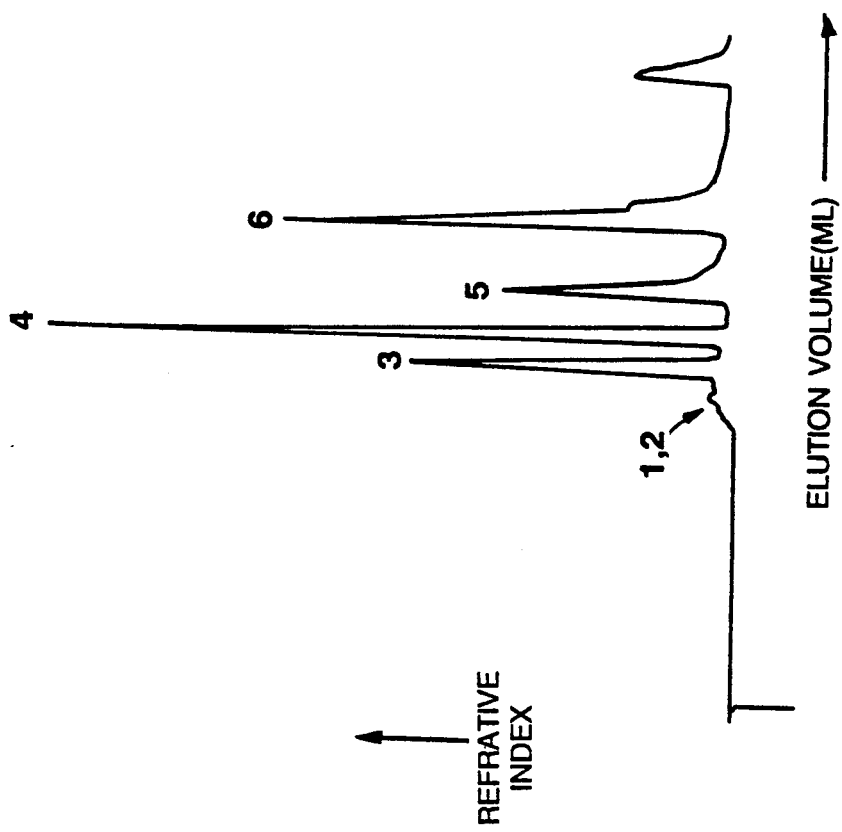

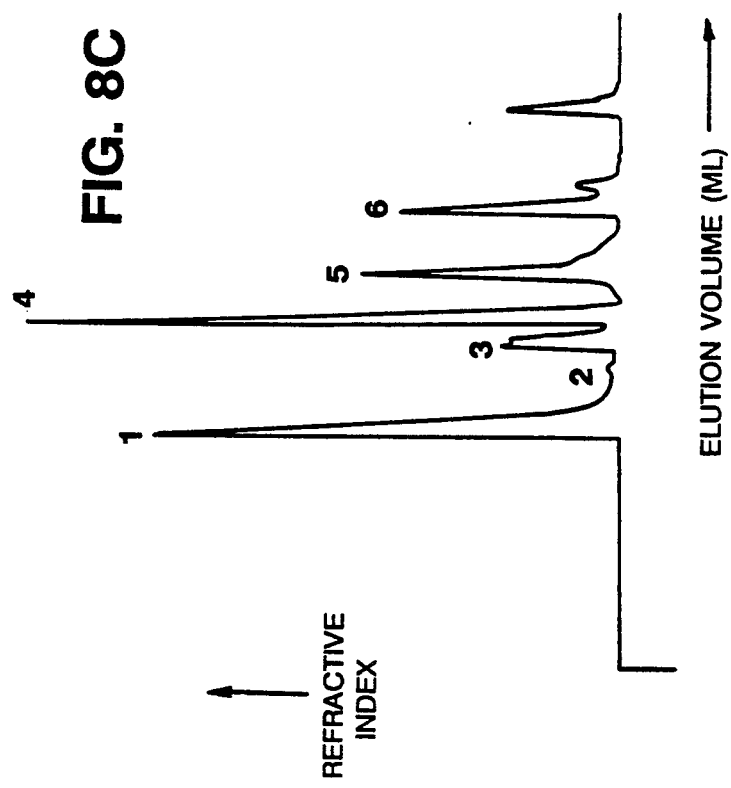
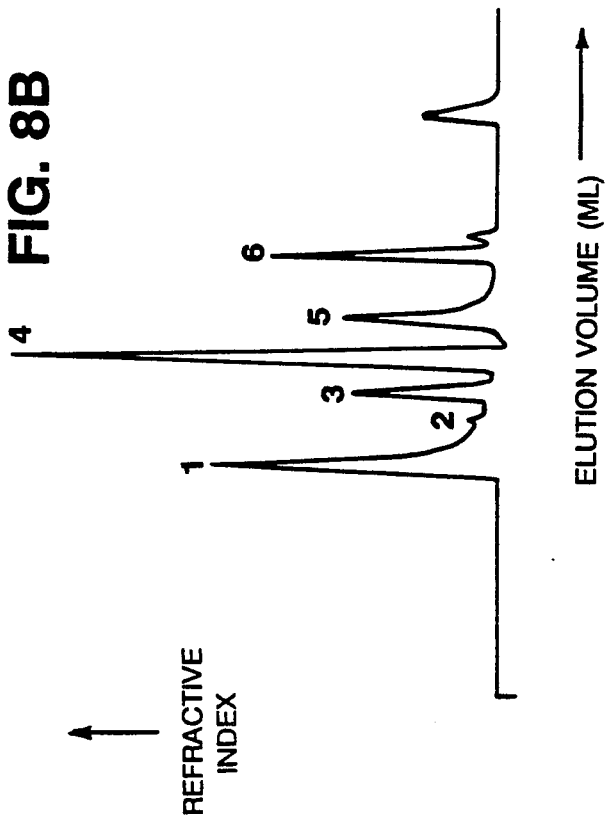

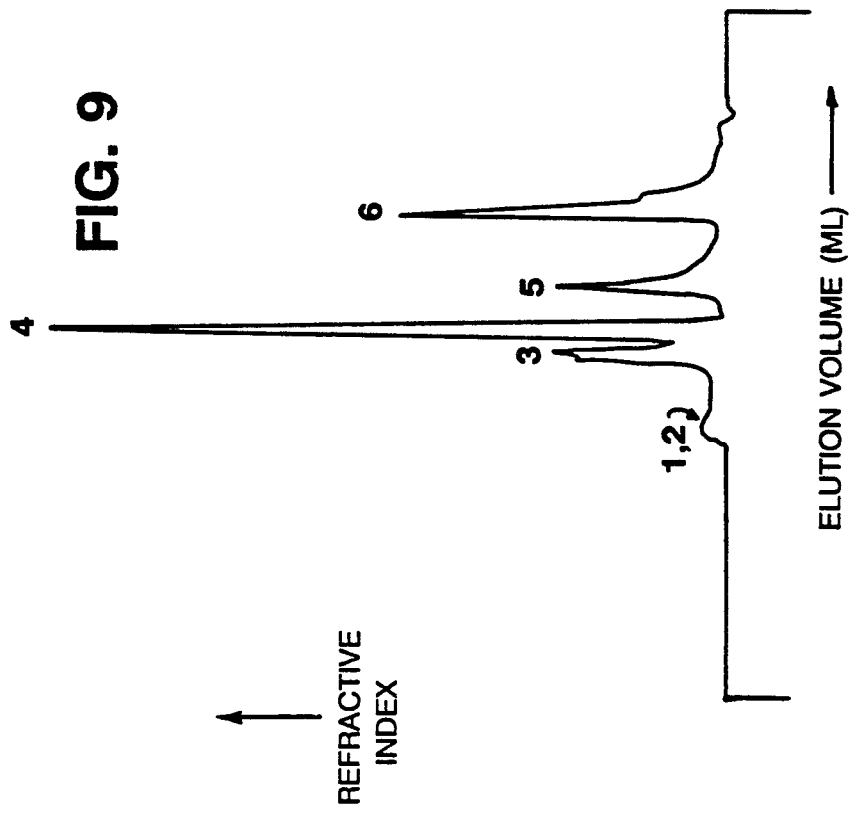
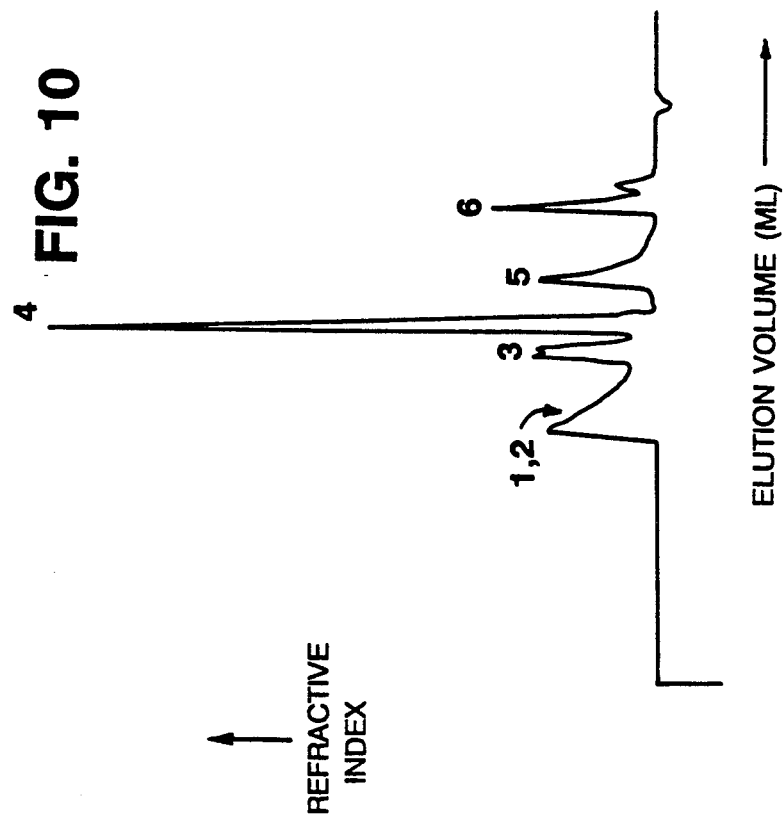

ANTIPERSPIRANT AND METHOD OF MAKING SAME

This application is a continuation-in-part of application Ser. No. 07/336,675 filed Apr. 12, 1989 which is in turn a continuation-in-part of application Ser. No. 181,564 filed Apr. 14, 1988, both now abandoned.

BACKGROUND OF THE INVENTION

This invention relates to a method of providing improved antiperspirant effectiveness and stability for basic aluminum chloride compositions (also known as aluminum chlorhydroxide compositions) and to such improved compositions. It has hitherto been proposed to increase the antiperspirant effectiveness of aluminum chlorhydroxide by aging under specified conditions an aqueous solution containing the aluminum chlorhydroxide, as described in Gosling et al. U.S. Pat. No. 4,359,456 and in British Patent Application No. 2048229A until the solution exhibits specified characteristics. In the British application it is pointed out that the increased activity is the result of a group of complexes called $Al^{c'}$ characterized by having a diffusion constant in gel-permeation chromatography which is within the range generally found for the $Al^b$ group of complexes but which displays a complexing rate in the ferron test which is in the range of the $Al^c$ complexes and by having molecules which are less than 100 A in size in aqueous solution. The $Al^{c'}$ complexes thus prepared are stable in aqueous solution at concentrations in the range of 10% to 30%.

It has also been proposed to increase the antiperspirant effectiveness of aluminum chlorhydroxide compositions by including in them zirconyl hydroxy chloride, and further by subjecting aqueous solutions of such compositions to heating under certain conditions, then rapidly drying the solution to solid form. The product when dissolved in water loses its improved efficacy rapidly, within a matter of days. The present invention also provides a method for improving the stability or efficacy, of compositions containing both aluminum chlorhydroxide and zirconyl hydroxy chloride, and provides such improved compositions.

It has now been found that a large increase in antiperspirant effectiveness of basic aluminum chloride (or aluminum chlorhydroxide) is provided by mixing it with monosilicic acid in aqueous solution, the amount of the chloride being 5-20% by weight and the amount of monosilicic acid being 0.03 to 8% by weight, preferably 0.3 to 3%, based upon the weight of the total mixed solution. The molecular distribution characteristics of the basic aluminum chloride immediately begin to change as determined by size exclusion (SE) chromatography, and at the same time the antiperspirant effectiveness begins to improve; the improvement continues at a gradually decreasing rate at room temperature for a period of a week or more, after which the composition retains its improved efficacy indefinitely, whether the composition is in the form of an aqueous solution or whether it is dried to a solid by removing the solvent. In dry solid form the composition contains basic aluminum chloride and silica in proportions as low as a few parts per million of the latter, based on the total.

The basic aluminum chloride may be added in dry powder form to the freshly prepared monosilicic acid aqueous solution with stirring, or if desired the basic aluminum chloride in aqueous solution may be mixed with the acid solution. The presence of zirconyl hydroxy chloride along with basic aluminum chloride either during or after treatment of the latter in accordance with the present invention is not deleterious. However, it is preferred to add the zirconyl hydroxy chloride after the basic aluminum chloride has been mixed with monosilicic acid in solution because if the zirconyl compound is introduced earlier the solutions mixture tends to gel, either immediately or within a limited time. In gel form the mixture is more difficult to process, e.g., by drying, into a form suitable for incorporating into a commercially preferred formulation. In some cases, however, for example when the monosilicic acid is prepared by hydrolysis of tetraethyl orthosilicate as described hereinafter, there is sufficient delay in the onset of gelation caused by the presence of zirconyl hydroxy chloride during the interaction between the basic aluminum chloride and the monosilicic acid so that there is adequate time to subject the solution to drying before it gels, thus providing the composition in stable dry, solid form.

Preferably the zirconyl hydroxy chloride, when introduced, is in the form of 5% to 25% by weight aqueous solution, although it can also be used in the form of a dry solid powder. The mixture of aluminum chlorhydroxide and monosilicic acid with which the zirconyl hydroxy chloride is mixed may also be either in the form of an aqueous solution or in dry solid form; the two solids may be mixed in powder form, or one or both may be in aqueous solution. Indeed, the zirconyl hydroxy chloride may be formed in situ by providing a mixture of aluminum chlorhydroxide and monosilicic acid having the desired molecular distribution characteristics and adding to it hydrochloric acid (and glycine if desired) and hereafter dissolving basic zirconium carbonate in the mixture. There is nothing critical about either the concentration of the zirconyl hydroxy chloride in solution or the Zr:Al atomic ratio, although at least about one atom of zirconium for each six atoms of aluminum is required to produce a substantial improvement in the antiperspirant effectiveness of the mixture of aluminum chlorohydroxide with monosilicic acid, and little or no further improvement is produced by increasing the amount of zirconium above one atom of zirconium for each atom of aluminum in the product. In addition, an anti-gelling agent in the form of a neutral amino acid such as glycine may be present, if desired, in either the mixture of aluminum hydroxychloride with monosilicic acid or in the solution of zirconyl hydroxy chloride. The presence of such an antigelling agent is not required, however. On the other hand, if the zirconyl hydroxy chloride is mixed with the aluminum chlorhydroxide before monosilicic acid is introduced, gelation occurs whether or not such an antigelling agent is present, making it difficult to obtain the product in the desired form.

The compositions of zirconyl hydroxy chloride and aluminum chlorhydroxide (basic aluminum chloride) which can be employed in the present invention include those in which the zirconyl compound has the formula $ZrO(OH)_xCl_y$ where $X+Y=2$ or a hydrate thereof and the aluminum compound has the formula $Al_2(OH)_{6-n}Cl_n$ where n is from 0.8 to 2 or a hydrate thereof, n preferably being 1. The atomic proportion of zirconium to aluminum in the composition may vary from about 0:1 to 1:1, and as pointed out above is preferably from 1:1 to 1:6. The atomic proportion of metal to chloride may vary from about 0.9 to 1.9. The inclusion in the composition of a neutral amino acid as described in Grad U.S. Pat. No. 2,854,382, which patent is incorporated herein by reference, does not have an adverse effect upon the formation of the desired novel complex. Commercially available compositions of zirconyl hydroxy chloride and aluminum chlorhydroxide mixtures frequently contain glycine as the neutral amino acid in an amount such that the molar ratio of glycine to zirconyl hydroxy chloride is about 1:1. The glycine or other neutral amino acid aids in preventing gelation of the aqueous solution before or during the heating step of the method of the present invention; and its presence does not prevent formation of the desired complex and does not interfere with the conversion of the heated solution to solid form nor with the subsequent use of the solid as an antiperspirant.

The monosilicic acid in solution should be freshly prepared; by this is meant an aqueous solution containing the acid in dissolved form, substantially free from precipitate and from gel. The precise amount of monosilicic acid required to convert conventional basic aluminum chloride to the new form having greatly enhanced antiperspirant effectiveness varies depending not only upon the concentration of the chloride but upon the procedure used to prepare the monosilicic acid solution and upon the length of time elapsing between its preparation and its use. For optimum results, the solution of monosilicic acid should be used as soon as possible after its preparation. Depending upon temperature of storage as well as upon pH and concentration, the monosilicic acid solution tends to lose its effectiveness after storage for a few days or weeks, presumably because of progressive polymerization of the monosilicic acid. Water-insoluble or precipitated silica, e.g., colloidal silica, or silica gel, is ineffective for the purpose of this invention, as is an alkaline solution of a silicate such as sodium silicate.

It has been reported in the prior art that freshly prepared aqueous solutions of silicic acid exist in "true solution". See Otterstedt et al., J. Colloid and Interface, Sci., Vol. 115(1), 95-103 (1987) and Iler et al., J. Phys. Chem., Vol. 57, 604 (1953). These solutions are initially composed of monomeric silicic acid units. The species encountered in these solutions appear to be labile and changes in concentration or pH are followed by rapid changes in species distribution and polymerization. The silicic acid will eventually precipitate as silica until the soluble species are reduced to about $10^{-3}$M (the solubility constant for amorphous silica).

The rate of silica formation and precipitation depends upon initial concentration of the monosilicic acid in solution, pH, temperature, the presence of cations other than hydrogen, and the presence of miscible solvent other than water, such as lower alkanols. Increases in any of the foregoing except the last tend to increase the instability of the solution and accelerate precipitation or gel formation. The presence of basic aluminum chloride dissolved in the solution of monosilicic acid increases the pH to about 3.5 to 4.

While applicants do not wish to be bound to a particular theory of interaction between the basic aluminum chloride and monosilicic acid, it is believed that competition between the monosilicic acid and the basic aluminum chloride for hydroxide ions in aqueous solution at a pH from 2 to 4, when the solution contains a very low concentration of free hydroxide ions, causes redistribution in the basic aluminum chloride to provide the molecular form which displays increased antiperspirant effectiveness.

The monosilicic acid solution can be prepared by various conventional procedures, such as the one described in Alexander, J. Am. Chem. Soc., Vol. 75, pp. 2887-8 (1953). In one preferred embodiment of the invention it is prepared by treating an aqueous solution of soluble silicate salt such as sodium or potassium silicate with a water-insoluble cation exchange resin in its hydrogen form as described, for example, in U.S. Pat. No. 2,588,389. In another preferred embodiment it is prepared by hydrolysis of tetraethyl orthosilicate. Mixing or stirring of tetraethyl orthosilicate with water at room temperature suffices to produce hydrolysis, but heating accelerates the hydrolysis as does the addition of an acid, e.g., a mineral acid such as hydrochloric.

The basic aluminum chloride may be added in dry powder form to the freshly prepared monosilicic acid aqueous solution with stirring, or if desired the basic aluminum chloride in aqueous solution may be mixed with the acid solution.

The time required to achieve optimum conversion of basic aluminum chloride to the desired product after mixing with an aqueous monosilicic acid solution may vary from several hours to several weeks, depending upon the nature of the preparation of the monosilicic acid, the extent and conditions of its storage before use; and the relative concentrations of monosilicic acid and of the basic aluminum chloride. The temperature may range from 5° to 100° C., preferably from room temperature to 80° C. as shown in the examples. The zirconyl hydroxy chloride component optionally may be added after the desired conversion, after which the product may be treated in the same way as the product containing no zirconium hydroxy chloride.

Once the desired conversion has been achieved, the water and other volatile components such as alcohol, if present, may be evaporated if desired. The length of time the solution is allowed to stand before drying, as well as the speed of drying are not critical since the product continues to maintain indefinitely its superior antiperspirant effectiveness, once attained, whether it is in solution or in the form of dry particles, and at moderately elevated temperatures as well as at lower temperatures, even below 0° C. If colloidal or precipitated material has formed in the mixed solution it may be removed by filtration for example, although some decrease in antiperspirant effectiveness may result, whether or not the composition is subsequently dried to solid form.

If a product containing both zirconium and aluminum is desired, an aqueous solution of zirconyl hydroxy chloride, with or without an antigelling neutral amino acid such as glycine, may be mixed with the dry solid product containing aluminum chlorhydroxide and monosilicic acid. Even after filtration residual silicic acid remains in the composition, either in the form of monosilicic acid or as its polymerization products although its amount is greatly reduced from the proportion present in the initial mixture of basic aluminum chloride and monosilicic acid and may even be as low as of the order of parts per million of the basic aluminum chloride. The addition of colloidal silica or silica gel to the composition has no effect upon the antiperspirant effectiveness of the composition.

BRIEF DESCRIPTION OF DRAWINGS

FIG. 7 shows a chromatogram of the product of Example 5 of the present invention;

FIG. 8A, 8B, and 8C show chromatograms of the product of Example 6 of the present invention;

FIG. 9 shows a chromatogram of the product of Example 7 of the present invention;

FIG. 10 shows a chromatogram of the product of Example 8 of the present invention;

Figure 1:
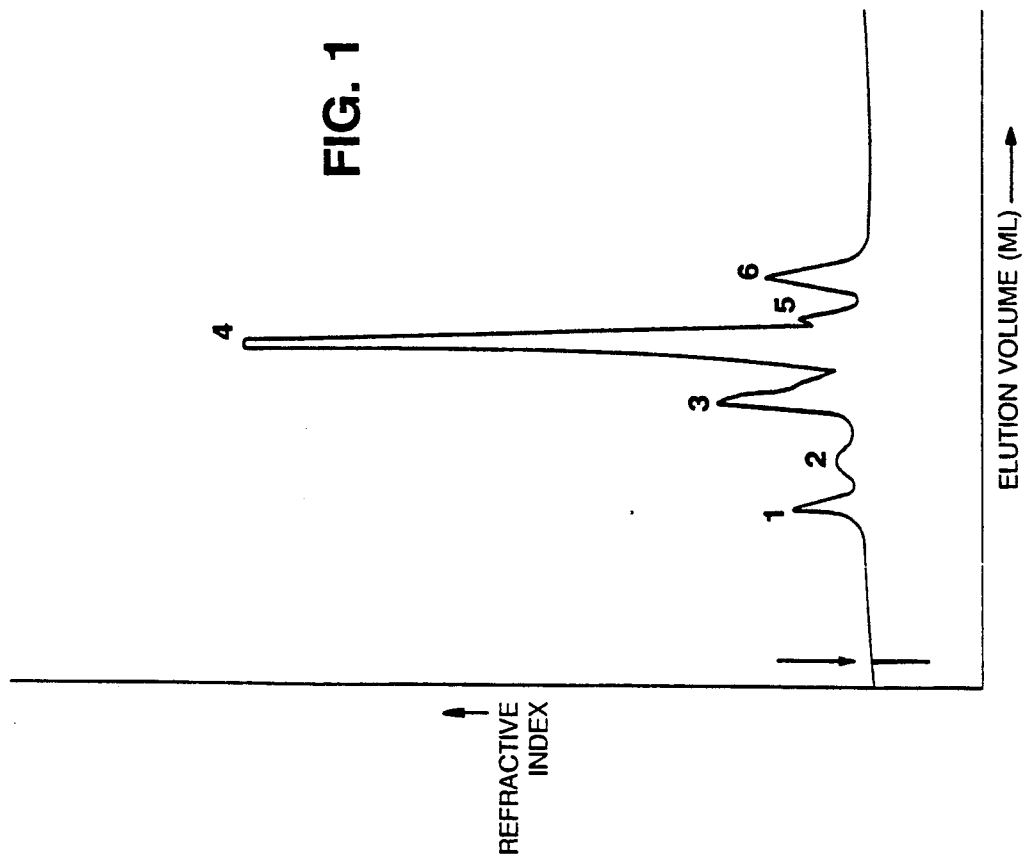
FIG. 1 shows a generalized chromatogram of a representative product of the present invention.

The new product having superior antiperspirant effectiveness is characterized and distinguished from other forms of basic aluminum chloride of relatively low antiperspirant effectiveness by its size exclusion chromatogram, its silicic acid content, and by the fact that its antiperspirant effectiveness does not decrease in contact with water. The product containing zirconyl hydroxy chloride is distinguished in the same way. The chromatogram is obtained by subjecting to size exclusion chromatography a specimen of a water solution containing approximately 10% by weight of the basic aluminum chloride and silicic acid. The solution is filtered through a membrane filter having 0.45 $\mu$m diameter pores, then applied to a size exclusion (SE) column and eluted, and the refractive index of successive fractions of the eluent as it leaves the column is measured and plotted against the cumulative total volume of eluent to provide the chromatogram. Each peak in the chromatogram indicates the presence of a different molecular size component of the solution in the fraction of eluent being measured. A representative chromatogram of the product of the present invention on a column of Sephadex G-50 (as defined below) is illustrated in FIG. 1, in which the fraction exhibiting the first peak (1) contains colloidal silica. Most products will show only a very small peak 1 because most of the free silica precipitates and is removed by the filtration step prior to chromatography. In some cases this peak can be resolved into two or more separate peaks. The fractions of peaks 2-5 all contain aluminum compounds. Peak 2 fraction contains unchanged or residual basic aluminum chloride. Peak 3 and 4 fractions together contain at least 80% of the total aluminum compounds present in the specimen and display improved antiperspirant effectiveness as compared to the starting material of peak 2; peak 4 is at least twice the height of peak 3, preferably four times as high or higher. The relative heights of the peaks 3 and 4 are proportional to the relative amounts of material in the fractions marked by each peak. Peak 3 typically exhibits a "shoulder" as seen in FIG. 1, indicating the presence of two somewhat different material fractions present in this peak 3. Under some circumstances it is possible to obtain sufficiently high resolution during chromatography so that peak 3 is resolved into more than a single peak, in which case the highest of the peaks within the range of K values (as defined hereinafter) for the fraction of peak 3, is the reference for comparing with the height of the highest peak within the range of K values for peak 4; the height of the latter is at least twice that of the former. Alternatively, since the area beneath each peak of the chromatogram is proportional to the amount of the material fraction represented by that peak, the total areas beneath all of the peaks within the K values for peak 4 may be compared with the total areas beneath all of the peaks within the K values for peak 3. In this case the total area for the first (i.e., the total amount of the peak 4 fraction) is at least twice as great as the total area for the second (i.e., the total amount of the peak 3 fraction) in the compositions of the present invention.

Figure 5:
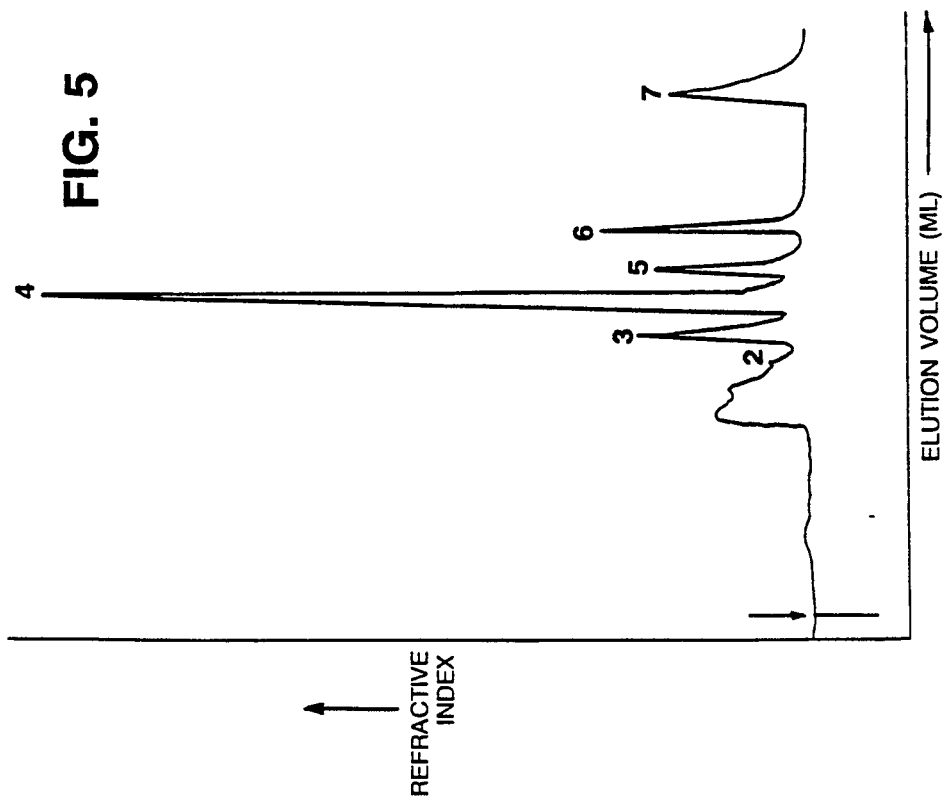
FIG. 5 shows a chromatogram of the product of Example 3 of the present invention.

Peak 5 fraction contains low molecular weight aluminum species sometimes present in commercially available basic aluminum chloride; the height of peak 5 increases with decrease in the pH of the eluent, but it remains a minor component in every case. Peak 6 fraction contains little or no aluminum. Some of the peaks, particularly those displaying shoulders, may be separated into two or more peaks by increasing the resolution of the chromatograph. When other ingredients are present, such as the ethyl alcohol by-product of hydrolysis of tetraethyl orthosilicate, they may form additional peaks, as shown in the chromatogram of FIG. 5, depending upon the column used.

The location of the fractions of peaks 3 and 4 of any specimen can be identified in terms of the distribution constant or value, defined as:

$$K = \frac{V - V_e}{V_t - V_e}$$

where:

V = Volume of eluent which has passed through the column at the point at which the particular peak appears on the chromatogram.

$V_e$ = Volume of eluent which has passed at the point at which the "excluded peak" appears on the chromatogram. The "excluded peak" which is peak 1 of FIG. 1, contains all of the material of the specimen being examined which is larger than the size exclusion limit of the packing material of the column.

$V_t$ = Volume which has proceeded through the column at the point at which the "totally included" peak appears; the totally included peak (peak 6 of FIG. 1) contains the material of the specimen being examined which is of such a molecular size that it is totally included in the pore volume of the column.

These K values will vary with the type of column material and eluent used. For example, the following column materials can be used:

A. porous spherical silica particles approximately 5-7 $\mu$m in diameter having a pore diameter of 10 nm (for example, Nucleosil 100-5 or 100-7 from Machery Nagel);

B. silica with glycerylpropyl bonded phase particles approximately 5 $\mu$m in diameter having a pore diameter of 6 nm and having a molecular weight range of 20,000 (excluded) to 300 (included) for globular proteins (for example, Synchropak GPC-60 from Synchron, Inc.);

C. a cross-linked dextran having a molecular weight range of 30,000 (excluded) to 1000 (included) for globular proteins (for example, Sephadex G50).

The eluents for the three columns are as follows:

Column A: 0.01 M aqueous nitric acid

Column B: 0.1 M aqueous potassium chloride adjusted to pH 4.5 with hydrochloric acid Column C: 0.1 M aqueous potassium chloride adjusted to pH 3 with hydrochloric acid The K values for the two peaks indicating the fractions which are characteristic of the new products are as follows for the three columns and eluents:

A. 0.30–0.40 and 0.49–0.53
B. 0.27–0.29 and 0.31–0.34
C. 0.47–0.53 and 0.68–0.72

In each case, the height of the peak having the larger K value is at least twice the height of the other in all of the products of the present invention. Column dimensions, specimen size, and eluent flow rate depend on the system used. In the case of column A, length was 50 cm, diameter 4.6 mm stainless steel, specimen size was 2–4 $\mu$L, and eluent flow rate was 0.5–0.75 mL/min. For column B, length was 30 cm, diameter 4.6 mm stainless steel, specimen size was 2 $\mu$L, and eluent flow rate was 0.4 ml/min. For column C, length was 96 cm, diameter 9 mm glass, specimen size was 100 $\mu$L, and eluent flow rate was 0.2 ml/min.

The stability of the product of the present invention is such that its effectiveness as an antiperspirant does not decrease when it is stored either in dry solid form or as an aqueous solution; an improvement in antiperspirant effectiveness of the aqueous solution does occur during a period of the first week or more at room temperature after initial mixing of basic aluminum chloride with monosilicic acid solution, however, but at a decreasing rate, so that once it has reached maximum effectiveness it remains unchanged during further storage in either dry form or as an aqueous solution for several months or more at room temperature. This stability is reflected also in the chromatogram of the product; although the ratio of the height of peak 4 to that of peak 3 in FIG. 1 increases when the product remains in aqueous solution at room temperature, the rate of increase slows with the lapse of time after preparation of the mixed solution. When the product is in dry solid form it remains unchanged indefinitely at room temperature; water solutions made from the dry solid display the same chromatogram and same antiperspirant effectiveness regardless of the length of time the solid product has been stored. Consequently, the products of the present invention display high antiperspirant efficacy without decrease in contact with water; they also display, in solution in water at approximately 10% by weight, a chromatogram in which the ratio of the height of peak 4 to that of peak 3 does not decrease.

The high stability of the product of the present invention both in dry solid form and, within a few hours after the initial mixing step, in the form of an aqueous solution, makes it possible to incorporate it as the principal or sole active antiperspirant agent in a wide variety of conventional formulations including powders, creams, sticks, solutions, and dispersions or emulsions, including aerosol compositions. The formulations may be dispensed from any conventional containers such as roll-on applicators, aerosol cans, and solid stick containers. Once the composition has been dried, it is desirable to avoid using more than about 1.5–2% ethyl alcohol in formulations containing it because the alcohol tends to cause a decrease in antiperspirant effectiveness as shown by a change in the chromatogram.

Typical antiperspirant formulations in which the material of the present invention may be practically employed in anhydrous form are as follows:

| | Weight % |
|---|---|
| I. Non-aqueous Roll-On | |
| Finely divided solid of present invention | 20.0 |
| Quaternium-18 Hectorite | 2.7 |
| Anhydrous Alcohol SDA-40 | 1.6 |
| $H_2O$ | 0.2 |
| Cyclomethicone, a silicone oil | 75.5 |
| Perfume | q.s |
| II. Stick Antiperspirant | |
| Finely divided solid of present invention | 23.0 |
| Ozokerite Wax | 22.4 |
| Myristyl Alcohol | 17.2 |
| Cyclomethicone | 17.9 |
| PPG-15 Stearyl ether | 11.5 |
| Stearth-15 | 2.3 |
| Bentone Gel IPM | 5.7 |
| Perfume | q.s |
| III. Aerosol Antiperspirant | |
| Finely divided solid of present invention | 6.8 |
| Propylene carbonate | 0.3 |
| Quaternium-18 Hectorite | 1.0 |
| Cyclomethicone | 12.4 |
| Isopropyl myristate | 2.0 |
| Perfume | 0.6 |
| Propellant-A31 | 76.9 |

In addition, the anhydrous solid of the present invention can be replaced by an aqueous solution of the material, as, for example, in the following case:

| IV. Aqueous Roll-On | Weight % |
|---|---|
| Material of the present invention as a 15% aqueous solution | 73.0 |
| Cyclomethicone | 20.0 |
| Steareth-2 | 2.2 |
| Steareth-21 | 1.0 |
| PPG-15 Stearyl ether | 1.8 |
| Aluminum Starch Octenyl succinate | 2.0 |

In general, in antiperspirant compositions in which the products of the present invention are dispersed or dissolved in a pharmacologically and dermatologically acceptable vehicle or carrier, the amount of the products, whether in solid form or in the form of an aqueous solution, may vary from about 3% to 30% or even more based on the total weight of the composition.

The following specific examples are intended to illustrate more fully the nature of the present invention without acting as a limitation upon its scope.

EXAMPLE 1

A 200 g portion of ion-exchange resin (Dowex HCR-S) water and air-dried. The resulting cationic exchange resin was slurried in 300 ml of 0.05 M hydrochloric acid and cooled to below 10° C. in a water-ice bath. There was dissolved in the slurry 12 g of sodium metasilicate nonahydrate ($Na_2SiO_3.9H_2O$) in the form of finely ground powder. The exchange resin was then removed by filtration leaving a clear solution of monosilicic acid approximately 0.14 M in concentration at a pH of 2.2. To a 270 g portion of the solution was added a 30 g portion of basic aluminum chloride in dry powder form prepared by heating a 10% solution of basic aluminum chloride in water at 80° C. for 16 hours and spray drying, as described in UK patent Application 2,048,229A published Dec. 10, 1980. The resulting mixed solution containing 10% by weight of basic aluminum chloride was allowed to stand at room temperature for 48 hours.

Figure 2:
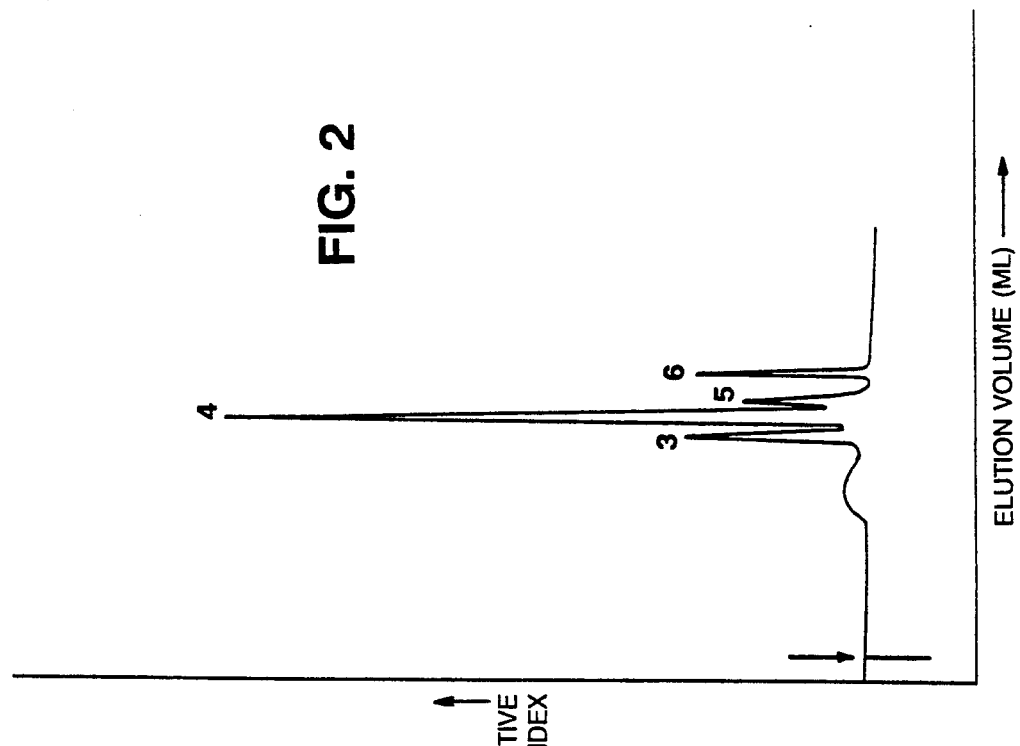
FIG. 2 shows a chromatogram of the product of Example 1 of the present invention.

An aliquot of the solution was filtered through a membrane having 0.45 μm diameter pores and was then subjected to SE HPLC on a column containing Nucleosil 100-7 using as eluent 0.01 M nitric acid and measuring refractive index. The resulting chromatogram is shown in FIG. 2 of the drawing, the second principal peak (4) having a height approximately 3.3 times that of the first (3).

Figure 3:
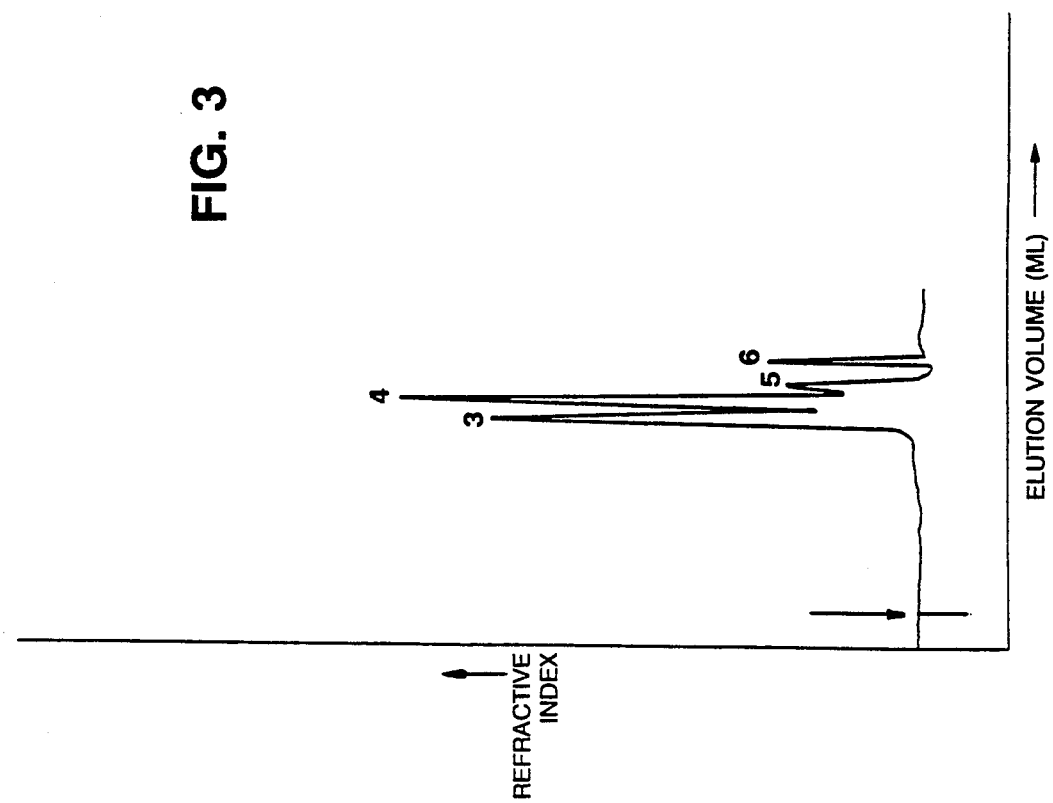
FIG. 3 shows a chromatogram of the basic aluminum chloride starting material used in Example 1.

As a control another 30 g portion of the same basic aluminum chloride dry powder starting material was dissolved in 270 g distilled water, allowed to stand 48 hours at room temperature, and subjected to SE HPLC at intervals under the same conditions as above. The ratio of the height of peak 4 to that of peak 3 decreased from the initial value. The chromatogram of the resulting solution is shown in FIG. 3, in which the ratio of the height of the second peak to that of the first is approximately 1.2:1.

Separate aliquots of the two solutions were tested for sweat reduction effectiveness on a panel of test subjects under standard conditions. The solution of the product of the invention was found to be significantly more effective than the control solution.

EXAMPLE 2

A slurry of cation-exchange resin in 0.05 M hydrochloric acid was prepared as described in Example 1 and cooled to below 10° C. To the slurry was added slowly with stirring 30.6 g of finely ground sodium metasilicate nonahydrate and allowed to dissolve; the slurry was then filtered to remove the resin and provide a solution of monosilicic acid approximately 0.27 M in concentration.

Figure 6:
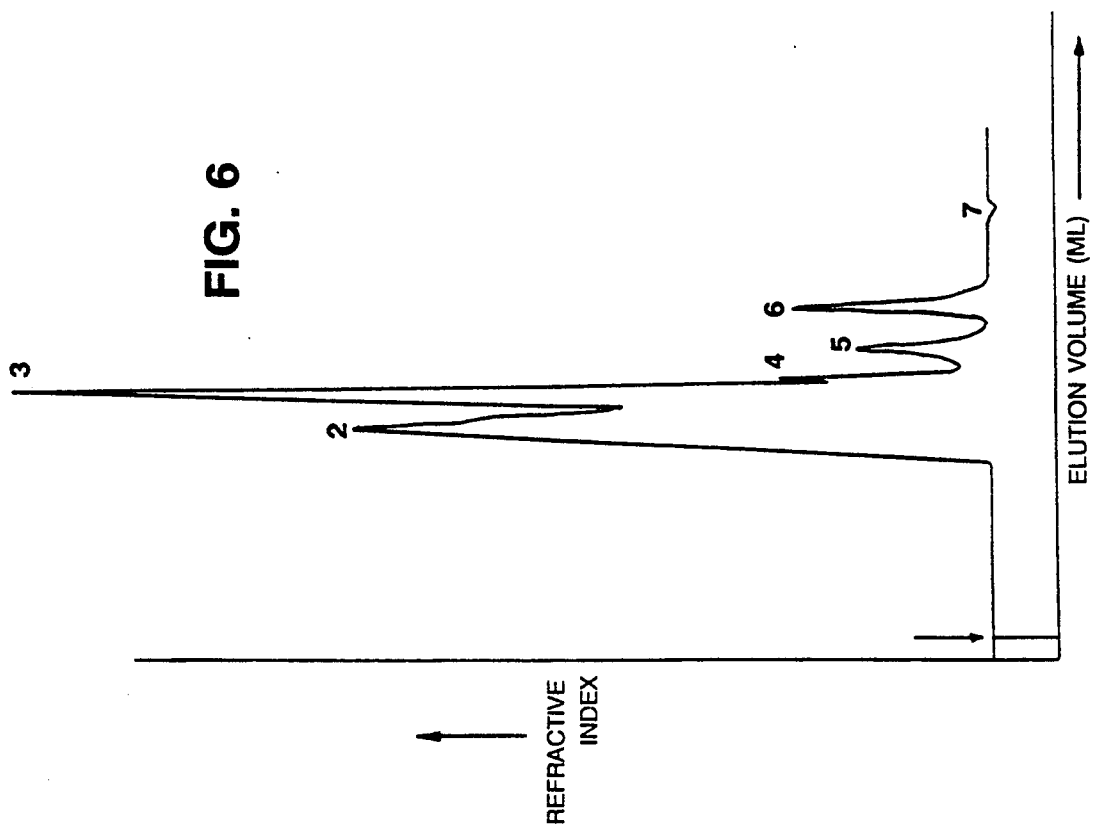
FIG. 6 shows a chromatogram of the basic aluminum chloride starting material used in Examples 2, 3 and 4.

Commercially available basic aluminum chloride was dissolved in water to provide a 50% by weight solution. An aliquot of this solution, after dilution to approximately 10% by weight, exhibited the chromatogram shown in FIG. 6 in which the ratio of the height of peak 4 to that of peak 3 is approximately 0.23:1.

Figure 4:
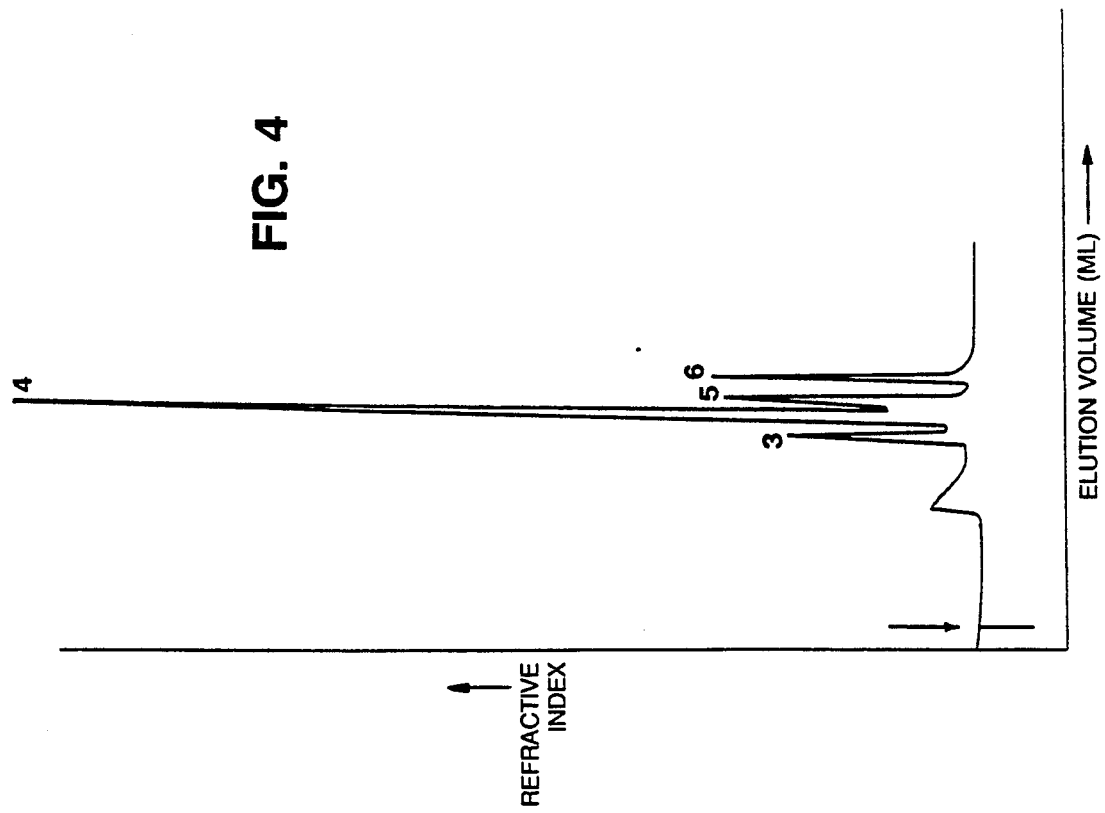
FIG. 4 shows a chromatogram of the product of Example 2 of the present invention.

Into 64 g of the monosilicic acid solution there was mixed by stirring 16 g of the 50% basic aluminum chloride solution and the mixture was allowed to warm to room temperature. After many days a portion was subjected to SE HPLC as described in Example 1 and was found to exhibit the chromatogram shown in FIG. 4 in which the height of the second principal peak (4) was approximately 5 times that of the first (3).

The mixture, in the form of an aqueous solution, exhibited significantly more antiperspirant effectiveness than did an aqueous solution containing the same concentration of commercially available basic aluminum chloride alone. It was essentially equal in antiperspirant effectiveness to an aqueous solution containing dissolved commercially available basic aluminum chloride together with zirconyl hydroxy chloride (atomic ratio of Al:Zr approximately 3.6 to 1) and glycine as an antigelling agent.

EXAMPLE 3

There were dissolved in 100 g of water 100 g of the same basic aluminum chloride used as starting material in Example 2. This solution was mixed with 750 ml of distilled water; 42.8 ml of tetraethyl-orthosilicate [TEOS] (Reagent grade, Fisher Scientific Co.) were added to the mixed solution, and the mixture was stirred for four weeks at room temperature. The solution became viscous and opaque after a couple of weeks due to the formation of a silica sol.

An HPLC chromatogram of the final product after filtration through a 0.45 μm pore diameter filter is shown in FIG. 5. The peak height ratio of peak 4 to peak 3 (the peaks of interest) is 4.4. In this case the peak preceding peak 2 is resolved into two peaks, both containing colloidal silica of such small particle size that it was not removed by the filtration step. Peaks 5 and 6 are due to small aluminum species and chloride and do not change during the reaction. The last peak observed, peak 7, contains ethanol, a by-product of TEOS hydrolysis.

The above solution exhibited significantly more antiperspirant effectiveness than did an aqueous solution containing the same concentration of basic aluminum chloride prepared as described in U.K. Patent Application 2,048,229A published Dec. 10, 1980.

EXAMPLE 4

A water solution containing 50% by weight of commercially available basic aluminum chloride was prepared, and a 200 g portion was mixed with 780 grams of distilled water and 10 ml of 6 N HC1. The solution was heated for two and a half hours at 80° C. then 22 ml of tetraethylorthosilicate [TEOS] were added to the solution with continuous stirring and heating at 80° C. for another hour.

The resulting solution was slightly opaque; this solution was then spray dried to obtain a white powder. An SE HPLC chromatogram of the powder redissolved in water at a concentration of 10% by weight contained a peak 4 to peak 3 ratio of 2.2; and a chromatogram similar to that shown in FIG. 2. The ethanol peak was absent since the ethanol was evaporated during the spray drying process.

The powder obtained by this method when formulated in the non-aqueous roll-on formulation base described above exhibited significantly more antiperspirant effectiveness than did the same formulation base containing basic aluminum chloride powder prepared as described in U.K. Patent Application 2,048,229A.

EXAMPLE 5

There was dissolved 0.97 grams of glycine in 7.9 grams of zirconyl hydroxy chloride aqueous solution (obtained from Magnesium Electron Co.: zirconium concentration 14.9% by wgt.) To the solution was added 50 gms of a solution prepared as described in Example 1 above.

A HPLC chromatogram of this solution adjusted to a total solids concentration of 10% by weight and subjected to SE HPLC as described in Example 1 is shown in FIG. 7. The solution exhibited superior effectiveness in sweat reduction on a panel of test subjects as compared to a similar solution to which no silicic acid had been added.

EXAMPLE 6

The procedure of Example 5 was repeated except that no glycine was included. Characteristic chromatograms by the procedure of Example 1 are shown in FIG. 8 immediately after preparation (A), after 24 hours at room temperature (B) and after 13 months at room temperature (C). It will be noted that in the chromatogram of FIG. 8C, as well as in the chromatograms for the products of Examples 7 and 8 below the resolution is such that peak 3 is split into a doublet, both of which are considered as a single peak for the purpose of this invention.

EXAMPLE 7

A solution was prepared as in Example 5. The solution was then reduced to a solid by removal of water, and ground to a fine powder. In this case, the solution was dried in a glass tray under a stream of air at room temperature. An HPLC chromatogram, shown in FIG. 9, was obtained after dissolving this powder to form an aqueous 10% solution by weight of total solids. Substantially the same results are obtained by spray drying the solution.

EXAMPLE 8

A product was prepared as in Example 7 except that no glycine was included. A characteristic chromatogram is shown in FIG. 10. In this chromatogram, broad peak 2 contains zirconyl hydroxy chloride, peak 5 contains aluminum chloride, and peaks 6 and 7 are artifacts containing neither aluminum nor zirconium compounds. Substantially the same results are obtained by spray drying the solution.

EXAMPLE 9

There was dissolved in 18 ml of water 0.97 gms of glycine; to this was added 7.9 gms of zirconyl hydroxy chloride solution (Magnesium Electron Co. - Zr concentration 14.9% by wgt.) and the solutions were mixed.

Figure 11:
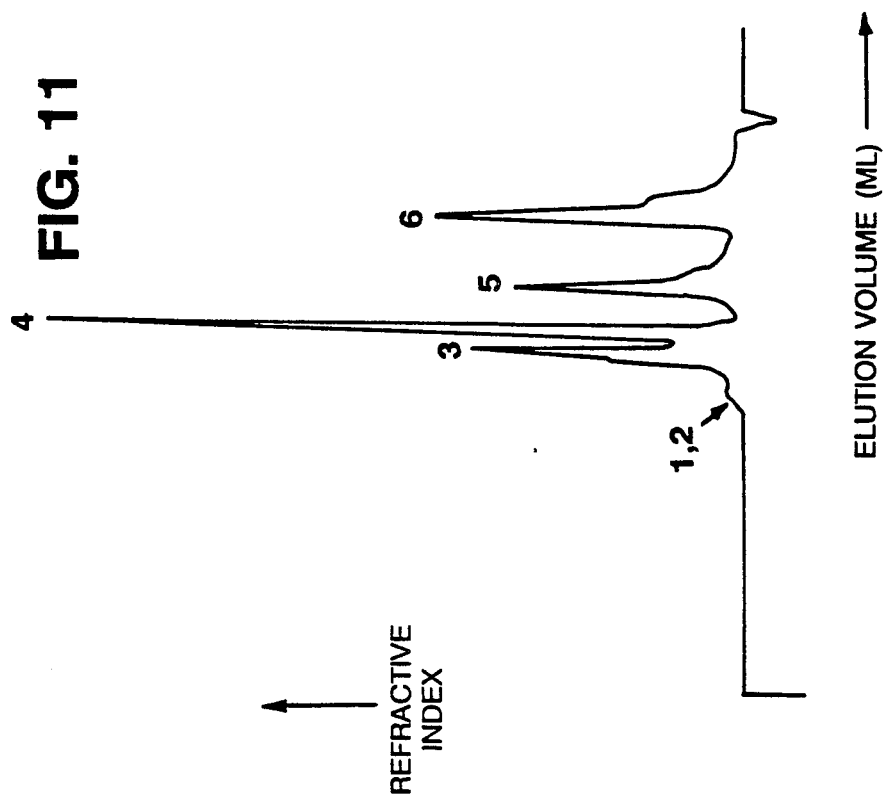
FIG. 11 shows a chromatogram of the product of Example 9 of the present invention.

There was added to the solution 5 gms of spray-dried powder (prepared as described in Example 4 above) and, immediately after dissolution, the resulting solution was evaporated to dryness at room temperature in a glass tray under a stream of air. The dried solid was then ground to a fine powder. A chromatogram obtained for a 10% solution of this powder is shown in FIG. 11. Substantially the same results are obtained by spray drying the solution.

EXAMPLE 10

Figure 12:
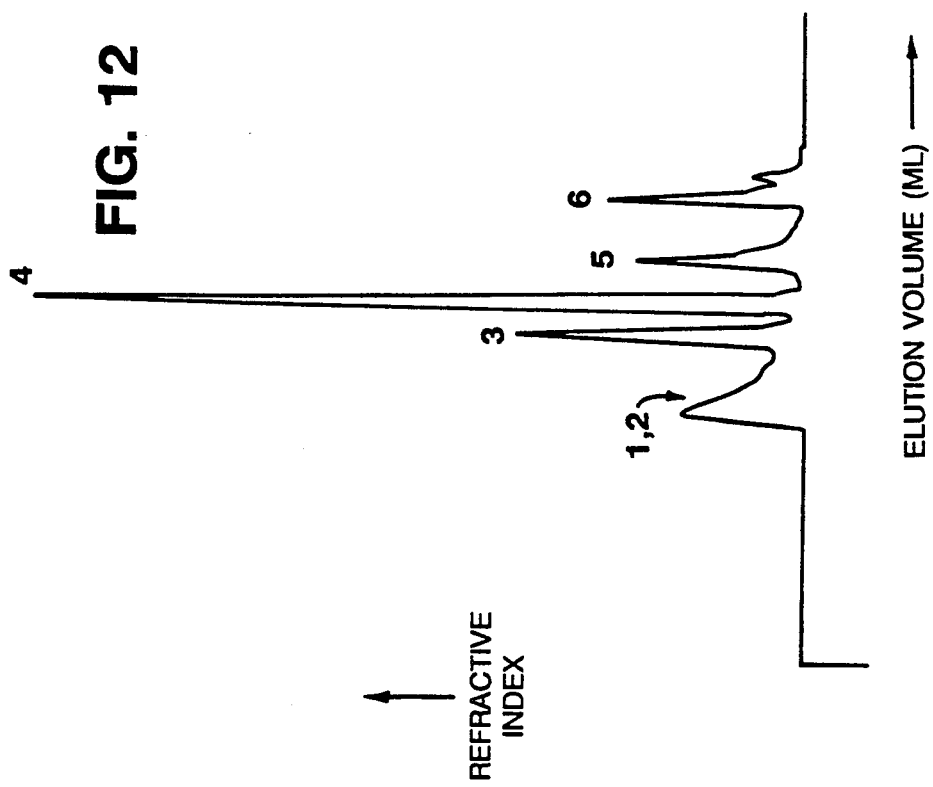
FIG. 12 shows a chromatogram of the product of Example 10 of the present invention.

A product was prepared as described in Example 9 except that no glycine was included. A chromatogram obtained for a 10% solution of this powder is shown in FIG. 12. Substantially the same results are obtained by spray drying the solution.

The solutions described in Examples 5 and 6 could be used in aqueous roll-on formulation such as the one described in formulation IV above. The powder prepared as described in Examples 7-10 could be used in formulations such as those of formulation I-III.

The tray drying of Examples 7-10 proceeds much more easily than in the case of the products of Examples 1-3, which adhere strongly to the tray and must be scraped off. The solutions of Examples 7-10, however, dry to a clear glass, which is much easier to collect and grind. However, the solutions of Examples 1-3 also dry to a friable glass if glycine is added to the solution prior to the drying step.

What is claimed is:

1. An antiperspirant composition comprising a dermatologically acceptable carrier and an effective amount of a basis aluminum chloride having high antiperspirant efficacy made by the process comprising mixing basic aluminum chloride with monosilicic acid in aqueous solution to increase the efficacy thereof.

2. An antiperspirant composition according to claim 1 wherein said basic aluminum chloride is dried after said mixing and prior to blending with said dermatologically acceptable carrier.

3. An antiperspirant composition according to claim 2 wherein said effective amount of basic aluminum chloride additionally comprises zirconyl hydroxy chloride which is added after the step of mixing said basic aluminum chloride with said monosilicic acid.

4. An antiperspirant composition according to claim 1 wherein during said mixing said basic aluminum chloride has a concentration of from 5% to 20% by weight, said monosilicic acid has a concentration of from 0.03% to 8% by weight, and said aqueous solution has a pH of from 2 to 4.

5. An antiperspirant composition according to claim 4 wherein during said mixing said monosilicic acid has a concentration of from 0.3% to 3% by weight.

6. An antiperspirant composition according to claim 5 wherein said mixing is conducted at a temperature of from room temperature to 80° C. for at least several hours.

7. An antiperspirant composition according to claim 6 wherein said monosilicic acid is prepared in situ by hydrolysis of tetraethylorthosilicate.

8. An antiperspirant composition according to claim 1, 4, 5, 6 or 7 additionally comprising zirconyl hydroxy chloride.

9. An antiperspirant composition according to claim 8 wherein said zirconyl hydroxy chloride is added after the step of mixing said basic aluminum chloride with said monosilicic acid.

* * * * *

UNITED STATES PATENT AND TRADEMARK OFFICE
CERTIFICATE OF CORRECTION

PATENT NO. : 5,330,751

DATED : July 19, 1994

INVENTOR(S) : Curtin et. al.

It is certified that error appears in the above-identified patent and that said Letters Patent is hereby corrected as shown below:

Title page, item (60), related U.S. Application Data, change "division" to -- continuation-in-part --.

Col. 12, line 14, change "basis" to -- basic --.

Signed and Sealed this

Twenty-seventh Day of September, 1994

Attest:

BRUCE LEHMAN

Attesting Officer

Commissioner of Patents and Trademarks